United States Patent
Callens et al.

(10) Patent No.: US 7,592,476 B2
(45) Date of Patent: Sep. 22, 2009

(54) PROCESS FOR PRODUCING ENANTIOPURE β-AMINO ACID DERIVATIVES, AND ENANTIOPURE β-AMINO ACID DERIVATIVES

(75) Inventors: Roland Callens, Grimbergen (BE); Marc Larcheveque, Paris (FR); Cyrille Pousset, Brussels (BE)

(73) Assignee: Solvay S.A. (BE)

( * ) Notice: Subject to any disclaimer, the term of this patent is extended or adjusted under 35 U.S.C. 154(b) by 229 days.

(21) Appl. No.: 10/551,723

(22) PCT Filed: Apr. 2, 2004

(86) PCT No.: PCT/EP2004/003688

§ 371 (c)(1),
(2), (4) Date: Feb. 14, 2006

(87) PCT Pub. No.: WO2004/087940

PCT Pub. Date: Oct. 14, 2004

(65) Prior Publication Data

US 2006/0211097 A1     Sep. 21, 2006

(30) Foreign Application Priority Data

Apr. 4, 2003   (FR) .................................. 03 04219

(51) Int. Cl.
 *C07C 229/00* (2006.01)
 *C07C 227/00* (2006.01)
(52) U.S. Cl. ........................................ 560/19; 562/554
(58) Field of Classification Search ........................ None
 See application file for complete search history.

(56) References Cited

U.S. PATENT DOCUMENTS

| 3,891,616 A | 6/1975 | Ondetti |
| 5,552,318 A | 9/1996 | Houng et al. |
| 2004/0029236 A1 * | 2/2004 | Groger et al. ............... 435/106 |
| 2005/0142646 A1 * | 6/2005 | Groger et al. ............... 435/106 |
| 2005/0170473 A1 * | 8/2005 | Miyata et al. ............... 435/106 |

FOREIGN PATENT DOCUMENTS

| EP | 0 605 033 | 7/1994 |
| WO | 9829561 | * 7/1998 |
| WO | WO-98/29561 | 7/1998 |

OTHER PUBLICATIONS

Forro et al., Mini-Reviews in Organic Chemistry (2004), 1(1), 93-102.*
Forro et al., Organic Letters (2003), 5(8), 1209-1212.*
Kanerva et al., Tetrahedron: Asymmetry (1996), 7(6), 1705-1716.*
Abstract, Dear et al., Xenobiotica (2000), 30(4), 407-426; CAS online citation 133:290626 [retrieved Dec. 6, 2008] from STN; Columbus, OH, USA.*

* cited by examiner

*Primary Examiner*—Karl J Puttlitz
(74) *Attorney, Agent, or Firm*—Connolly Bove Lodge & Hutz LLP

(57) ABSTRACT

Process for producing enantiopure β-amino acid derivatives corresponding to general formula (I) $R1-NZ-CHR2-CH_2-COOR3$ (I) in which R1 and R2 independently denote organic residues optionally forming a cyclic substituent, R3 denotes H or an organic residue, and Z represents H or an amino function-protecting group, comprising a step in which a mixture of enantiomers of a compound corresponding to general formula (II) $R1-NZ-CHR2-CH_2-COOR4$ (II) in which R1, R2 and Z are as defined for formula (I), and R4 is an organic residue, is subjected to hydrolysis in the presence of a lipase.

15 Claims, No Drawings

PROCESS FOR PRODUCING ENANTIOPURE β-AMINO ACID DERIVATIVES, AND ENANTIOPURE β-AMINO ACID DERIVATIVES

RELATED APPLICATIONS

This application is a national stage application (under 35 U.S.C. 371) of PCT/EP2004/003688 filed Apr. 2, 2004 which claims benefit to French application 03/04219 filed Apr. 4, 2003.

The present invention relates to a process for producing enantiopure β-amino acid derivatives, and to enantiopure β-amino acid derivatives.

Some β-amino acids and their derivatives are useful in the context of the production of peptides which can be used as medicinal products. Specific examples of such β-amino acids comprise at least one nitrogenous heterocycle.

In the search for active principles, it is desirable to have amino acids which participate in the pharmacological activity in particular peptides and which can be used in the process for producing peptides or peptide analogues.

U.S. Pat. No. 3,891,616 describes some biologically active peptides containing 2-pyrrolidineacetic acid. The N-Boc derivative of this acid is prepared by treatment of natural L-proline with diazomethane.

This known process requires the use of an enantiopure natural amino acid as starting product. The latter is subjected to conversions with a dangerous reagent under conditions which can involve a risk of racemization.

The invention is aimed at remedying the abovementioned problems.

The invention consequently relates to a process for producing enantiopure β-amino acid derivatives corresponding to general formula (I)

R1-NZ-CHR2-CH$_2$—COOR3     (I)

in which

R1 and R2 independently denote organic residues optionally forming a cyclic substituent, R3 denotes H or an organic residue, and Z represents H or an amino function-protecting group, comprising a step in which a mixture of enantiomers of a compound corresponding to general formula (II)

R1-NZ-CHR2-CH$_2$—COOR4     (II)

in which

R1, R2 and Z are as defined for formula (I), and

R4 is an organic residue, is subjected to hydrolysis in the presence of a lipase.

It has been found that the process according to the invention makes it possible to produce β-amino acids or their derivatives of high enantiomeric purity with a high yield.

The term "enantiopure compound" is intended to denote a chiral compound consisting essentially of an enantiomer. The enantiomeric excess (ee) is defined as: ee(%)=100(x$_1$−x$_2$)/(x$_1$+x$_2$) with x$_1$>x$_2$; x$_1$ and x$_2$ represent the content in the mixture of enantiomer 1 or 2 respectively.

The term "organic residue" is intended to denote in particular linear or branched alkyl or alkylene groups which may contain hetero atoms, such as in particular boron, silicon, nitrogen, oxygen or sulphur atoms, cycloalkyl groups, heterocycles and aromatic systems. The organic residue may contain double or triple bonds and functional groups.

The organic residue comprises at least 1 carbon atom. It often comprises at least 2 carbon atoms. It preferably comprises at least 3 carbon atoms. More particularly preferably, it comprises at least 5 carbon atoms.

The organic residue generally comprises at most 100 carbon atoms. It often comprises at most 50 carbon atoms. It preferably comprises at most 40 carbon atoms. More particularly preferably, it comprises at most 30 carbon atoms.

The term "alkyl group" is intended to denote in particular a linear or branched alkyl substituent comprising from 1 to 20 carbon atoms, preferably 1, 2, 3, 4, 5, 6, 7, 8, 9 or 10 carbon atoms. Specific examples of such substituents are methyl, ethyl, n-propyl, isopropyl, n-butyl, isobutyl, tert-butyl, n-pentyl, isopentyl, n-hexyl, 2-hexyl, n-heptyl, n-octyl and benzyl.

The term "cycloalkyl group" is intended to denote in particular a substituent comprising at least one saturated carbocycle containing 3 to 10 carbon atoms, preferably 5, 6 or 7 carbon atoms. Specific examples of such substituents are cyclopropyl, cyclobutyl, cyclopentyl, cyclohexyl and cycloheptyl.

The term "alkylene group" or "cycloalkylene group" is intended to denote in particular the divalent radicals derived from the alkyl or cycloalkyl groups as defined above.

When the organic residue contains one or optionally more double bonds, it is often chosen from an alkenyl or cycloalkenyl group comprising from 2 to 20 carbon atoms, preferably 2, 3, 4, 5, 6, 7, 8, 9 or 10 carbon atoms. Specific examples of such groups are vinyl, 1-allyl, 2-allyl, n-but-2-enyl, isobutenyl, 1,3-butadienyl, cyclopentenyl, cyclohexenyl and styryl.

When the organic residue contains one or optionally more triple bonds, it is often chosen from an alkinyl group comprising from 2 to 20 carbon atoms, preferably 2, 3, 4, 5, 6, 7, 8, 9 or 10 carbon atoms. Specific examples of such groups are ethinyl, 1-propinyl, 2-propinyl, n-but-2-inyl and 2-phenylethinyl.

When the organic residue contains one or optionally more aromatic systems, it is often an aryl group comprising from 6 to 24 carbon atoms, preferably from 6 to 12 carbon atoms. Specific examples of such groups are phenyl, 1-tolyl, 2-tolyl, 3-tolyl, xylyl, 1-naphthyl and 2-naphthyl.

The term "heterocycle" is intended to denote in particular a cyclic system comprising at least one saturated or unsaturated ring made up of 3, 4, 5, 6, 7 or 8 atoms, at least one of which is a hetero atom. The hetero atom is often chosen from B, N, O, Si P and S. It is more often chosen from N, O and S.

Specific examples of such heterocycles are aziridine, azetidine, pyrrolidine, piperidine, morpholine, 1,2,3,4-tetrahydroquinoline, 1,2,3,4-tetrahydroisoquinoline, perhydroquinoline, perhydroisoquinoline, isoxazolidine, pyrazoline, imidazoline, thiazoline, tetrahydrofuran, tetrahydrothiophene, pyran, tetrahydropyran and dioxane.

The organic residues as defined above may be unsubstituted or substituted with functional groups. The term "functional group" is intended to denote in particular a substituent comprising or consisting of a hetero atom. The hetero atom is often chosen from B, N, O, Al, Si, P, S, Sn, As and Se and the halogens. It is more often chosen from N, O, S and P, in particular N, O and S.

The functional group generally comprises 1, 2, 3, 4, 5 or 6 atoms.

By way of functional groups, mention may, for example, be made of halogens, a hydroxyl group, an alkoxy group, a mercapto group, an amino group, a nitro group, a carbonyl group, an acyl group, an optionally esterified carboxyl group, a carboxamide group, a urea group, a urethane group and the thiol derivatives of the abovementioned groups containing a carbonyl group, phosphine, phosphonate or phosphate groups, a sulphoxide group, a sulphone group and a sulphonate group.

In the process according to the invention, the substituent Z in the compound of general formula (I) or (II) is often an amino function-protecting group. In this case, an enantiopure β-amino acid derivative is obtained, as unreacted substrate, which can be used without further modification as a peptide synthesis intermediate.

By way of nonlimiting examples of amino function-protecting groups which may be represented by Z, mention may in particular be made of substituted or unsubstituted groups of alkyl or aralkyl type, such as the benzyl, diphenylmethyl, di(methoxyphenyl)methyl or triphenylmethyl (trityl) group, substituted or unsubstituted groups of acyl type, such as the formyl, acetyl, trifluoroacetyl, benzoyl or phthaloyl group, substituted or unsubstituted groups of aralkyloxycarbonyl type, such as the benzyloxycarbonyl, p-chlorobenzyloxycarbonyl, p-bromobenzyloxycarbonyl p-nitrobenzyloxycarbonyl, p-methoxybenzyloxycarbonyl, benzhydryloxycarbonyl, 2-(p-biphenylyl)isopropyloxycarbonyl, 2-(3,5-dimethoxyphenyl)isopropyloxycarbonyl, p-phenylazobenzyloxycarbonyl, triphenylphosphonoethyloxycarbonyl or 9-fluorenylmethyloxycarbonyl group, substituted or unsubstituted groups of alkyloxycarbonyl type, such as the tert-butyloxycarbonyl, tert-amyloxycarbonyl, diisopropylmethyloxycarbonyl, isopropyloxycarbonyl, ethyloxycarbonyl, allyloxycarbonyl, 2-methyl-sulphonylethyloxycarbonyl or 2,2,2-trichloroethyloxycarbonyl group, groups of cycloalkyloxycarbonyl type, such as the cyclopentyloxycarbonyl, cyclohexyloxy-carbonyl, adamantyloxycarbonyl or isobornyloxycarbonyl group, and groups containing a hetero atom, such as the benzenesulphonyl, p-toluenesulphonyl (tosyl), mesitylenesulphonyl, methoxytrimethylphenylsulphonyl, o-nitrophenylsulphenyl or trimethylsilane group.

Among these groups Z, those comprising a carbonyl group are preferred. The acyl, aralkyloxycarbonyl and alkyloxycarbonyl groups are more particularly preferred.

The protective group is preferably sterically hindering. The term "sterically hindering" is intended to denote in particular a substituent comprising at least 3 carbon atoms, in particular at least 4 carbon atoms, including at least one secondary, tertiary or quaternary carbon atom. The sterically hindering group often comprises at most 100, or even 50 carbon atoms. A protective group chosen from the alkoxy-carbonyl, aryloxycarbonyl and aralkoxycarbonyl groups is preferred. A tert-butyloxycarbonyl (BOC) group is most particularly preferred.

In the process according to the invention, the substituent R3 in the compound of general formula (I) is often a hydrogen atom. In this case, it is possible to replace it with organic residues as defined above, using processes known in themselves.

In the process according to the invention, the substituent R4 in the compound of general formula (II) is often an alkyl or cycloalkyl group as defined above. A methyl or ethyl group is preferred.

In a preferred aspect, the substituents R1 and R2 in the compounds of general formula (I) and (II) form a heterocycle with the group NZ-CH. Said heterocycle preferably comprises 4, 5, 6, 7 or 8 atoms. More particularly preferably, it comprises 5, 6 or 7 atoms.

In a variant of this aspect, the heterocycle comprises at least one additional hetero atom, preferably chosen from N, O and S. A heterocycle comprising at least one additional hetero atom chosen from N and O is more particularly preferred.

The invention also relates to the enantiopure β-amino acids or enantiopure β-amino acid derivatives in accordance with this aspect. The invention also' relates to a peptide or peptide analogue which can be obtained using, in the process for producing it, an enantiopure β-amino acid derivative according to the invention. The peptide coupling of the enantiopure β-amino acid derivatives according to the invention can be carried out according to techniques known in themselves.

More particularly preferably, the process according to the invention is applied to the production of an enantiopure β-amino acid derivative of formula (III)

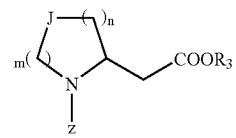

(III)

in which J is independently chosen from C, N, O and S; Z and R4 are as defined above, and m and n independently have the value 0 to 4. Preferably, m and n have the value 1, 2 or 3.

Specific examples of such enantiopure β-amino acid derivatives are chosen from the compounds below

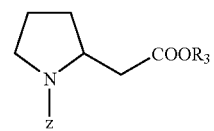

(IV)

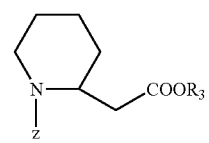

(V)

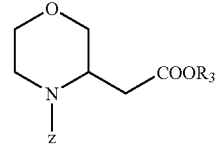

(VI)

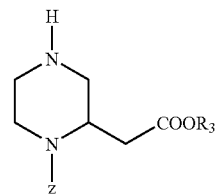

(VII)

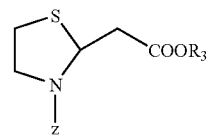

(VIII)

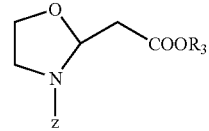

(IX)

in which Z and R3 are as defined above.

In the process according to the invention, the lipase is often chosen from *Pseudomonas cepacia* and *Candida antarctica* lipase. *Pseudomonas cepacia* lipase is preferred. The lipase can be used in free form or immobilized form, for example immobilized on a support such as ceramic.

In the process according to the invention, the hydrolysis is generally carried out at a temperature greater than or equal to 0° C. This temperature is often greater than or equal to 10° C. This temperature is preferably greater than or equal to 20° C. In the process according to the invention, the hydrolysis is generally carried out at a temperature less than or equal to 50° C. This temperature is often less than or equal to 40° C. This temperature is preferably less than or equal to 30° C.

In the process according to the invention, a pH greater than or equal to 6 is generally maintained during the hydrolysis. The pH is often greater than or equal to 6.5. A pH of approximately 7 is preferably maintained during the hydrolysis. In the process according to the invention, a pH less than or equal to 6 is generally maintained during the hydrolysis. The pH is often less than or equal to 7.5.

In the process according to the invention, the amount of lipase used is generally greater than or equal to 10 mg/mmol of compound of formula (II). This amount is preferably greater than or equal to 20 mg/mmol of compound of formula (II). In the process according to the invention, the amount of lipase used is generally less than or equal to 100 mg/mmol of compound of formula (II). This amount is preferably less than or equal to 50 mg/mmol of compound of formula (II).

The invention also relates to a process for producing a peptide or a peptide analogue, according to which
(a) an enantiopure β-amino acid derivative is produced according to the process of the invention;
(b) the enantiopure β-amino acid derivative obtained is used to produce the peptide or the peptide analogue.

The examples below are intended to illustrate the invention without, however, limiting it.

EXAMPLE 1

Synthesis of Enantiopure Derivatives of 3-carboxymethylmorpholine

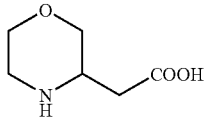

$C_6H_{11}NO_3$
M.: 145, 2 g. mol$^{-1}$

The racemic 3-carboxymethylmorpholine 1 was obtained, starting with morpholine, by successive steps of anodic methoxylation (electrochemical synthesis) of N-acetylated morpholine, substitution of the methoxy group with an allyl group by reaction with allyltrimethylsilane in the presence of TiCl$_4$, followed by oxidative ozonolysis.

1.1. Synthesis of 3-carbethoxymethylmorpholine hydrochloride

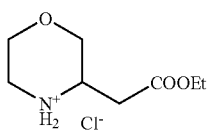

$C_8H_{16}ClNO_3$
M.: 209, 5 g. mol$^{-1}$ 0.85 ml of acetyl chloride was added dropwise to 10 ml of ethanol cooled to 0° C. A solution of β-amino acid 1 (4 mmol, 1 equiv.) in 3 ml of ethanol was then added and the mixture was brought to reflux for three hours. After evaporation of the solvents, 0.83 g of desired product was isolated (yield=98%).

$^{13}$C NMR:

δ (CDCl$_3$) 169.0 (s, COOEt), 67.5 (s, OCH$_2$CH), 63.5 (s, OCH$_2$CH$_2$), 61.6 (s, OCH$_2$CH$_3$), 51.2 (s, CHCH$_2$COOEt), 43.1 (s, CH$_2$NH), 33.1 (s, CHCH$_2$COOEt), 14.0 (s, OCH$_2$CH$_3$).

$^1$H NMR:

δ(CDCl$_3$) 4.18 (q, $^3J_{H-H}$=7.2 Hz, 2H, COOCH$_2$CH$_3$), 3-84-3.15 (m, 7H, CH$_2$CH$_2$OCH$_2$CH), 3.11 (dd, $^3J_{H-H}$=4.5 Hz, $^2J_{H-H}$=17.1 Hz, 1 Hz, 1H de CH$_2$CO$_2$Et), 2.79 (dd, $^3J_{H-H}$=7.9 Hz, $^2J_{H-H}$=17.1 Hz, 1H de CH$_2$CO$_2$Et), 1.26 (t, $^3J_{H-H}$=7.2 Hz, 3H, COOCH$_2$CH$_3$).

I.R.: (KBr) 3441 (νNH), 2954 (νNH), 1727 (νCO$_{ester}$).

Elemental Analysis:

Calculated: C 45.83%; H 7.69%; N 6.68%
Measured: C 42.13%; H 7.17%; N 6.66%

1.2. Synthesis of 4-tert-butoxycarbonyl-3-carbethoxymethylmorpholine

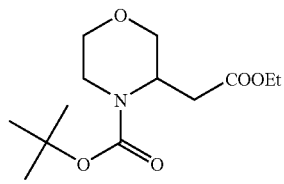

$C_{13}H_{23}NO_5$
M.: 273, 3 g. mol$^{-1}$ 2 g of sodium hydrogen carbonate (24 mmol, 4 equiv.) were added to a solution of 1.26 g of β-amino ester 2 (6 mmol) in 10 ml of THF and 35 ml of dioxane. When the solution had become homogenized, 1.75 g of tert-butyl pyrocarbonate (8 mmol), 1.3 equiv.) were added. The solution was heated for 5 h at 40° C. After evaporation, the residue was taken up in ether. The aqueous phase was extracted with 3 times 15 ml of ether. The organic phases were pooled and dried over magnesium sulphate. After evaporation of the organic phases, the residue was purified by chromatography on a silica column; eluent: 4/1 cyclohexane/ethyl acetate. 1.42 g of a solid corresponding to the expected product was isolated (yield=87%).

$^{13}$C NMR:

δ (CDCl$_3$) 171.3 (s, COOEt), 154.5 (s, NCOOt-Bu), 80.3 (s, C(CH$_2$)$_3$), 68.9 (s, OCH$_2$CH), 66.9 (s, OCH$_2$CH$_2$N), 60.7 (s, OCH$_2$CH$_3$), 48.1 (s, NCH), 39.5 (s, OCH$_2$CH$_2$N), 33.8 (s, CH$_2$COOEt), 28.4 (s, C(CH$_3$)$_3$), 14.2 (s, OCH$_2$CH$_3$).

$^1$H NMR:

δ (CDCl$_3$) 4.36 (large, 1H, NCH), 4.11 (q, $^3J_{H-H}$=7.1 Hz, 2H, OCH$_2$CH$_3$), 3.840 (m, 3H, 1H de OCH$_2$CH$_2$N, 1H de OCH$_2$CH$_2$N, 1H de OCH$_2$CH), 3.56 (dd, $^3J_{H-H}$=2.8 Hz, $^2J_{H-H}$=11.8 Hz, 1H, 1H de OCH$_2$CH), 3.43 (td, $^3J_{H-H}$=2.8 Hz, $^2J_{H-H}$=12 Hz, 1H, 1H de OCH$_2$CH$_2$N), 3.09 (m, 1H, 1H de OCH$_2$CH$_2$N), 2.81 (dd, $^3J_{H-H}$=8.8, Hz, $^2J_{H-H}$=15 Hz, 1H, 1H de CH$_2$COOEt), 2.54 (dd, $^3J_{H-H}$=5.5 Hz, $^2J_{H-H}$=15 Hz, 1H, 1H de CH$_2$COOEt), 1.44 (s, 9H, C(CH$_3$)$_3$), 1.25 (t, $^3J_{H-H}$=7.1 Hz, 3H, OCH$_2$CH$_3$).

Mass spectrometry:

M/Z (EI): 273 (1%) ((M)$^+$), 217 (5%) ((M-C$_4$H$_8$)$^+$), 200 (3%) ((M-CO$_2$CH$_2$CH$_3$)$^+$), 172 (24%) ((M-C$_5$H$_9$O$_2$)$^+$), 142 (43%), 130 (32%), 86 (46%), 57 (100%)((C$_4$H$_9^+$), 41 (26%).

I.R.: (pure) 1735 ($\nu CO_{ester}$), 1698 ($\nu CO_{carbamate}$).

Elemental Analysis:
Calculated: C 57.13%; H 8.48%; N 5.12%
Measured: C 57.06%; H 8.63%; N 5.04%

1.3. Enzymatic Racemate Cleavage of Racemic 4-tert-butoxycarbonyl-3-carbethoxymethylmorpholine 100 mg of Amano PS (*Pseudomonas cepacia*) enzyme were added to a solution of 273 mg of morpholine 3 (1 mmol) in 2 ml of THF, 8 ml of $10^{-2}$ M buffer solution, pH 7, and 8 ml of water. The reaction medium was stirred at 25° C. and the pH was maintained at pH 7, by means of an auto-titrator, by adding 0.1 N sodium hydroxide solution. The progression of the reaction was followed by virtue of the volume of 0.1 N sodium hydroxide added. After stirring for 10 hours and the addition of 5 ml of 0.1 N sodium hydroxide, the reaction medium was centrifuged in order to separate the solution from the enzyme. The solution was concentrated and the aqueous phase was extracted with ether. The organic phases were pooled and dried over magnesium sulphate. After evaporation, 125 mg of enantiopure 3b were obtained (yield=45%). The aqueous phase was acidified to pH 3 and was extracted with ether. The organic phases were pooled and dried over magnesium sulphate. After evaporation, 120 mg of enantiopure 4-tert-butoxycarbonyl-3-carboxymethylmorpholine 3a were obtained (yield=44%). The acid was recrystallized from a hexane/diisopropyl ether (8/2) mixture.

(3R)-4-tert-Butoxycarbonyl-3-carboxymethylmorpholine 3a

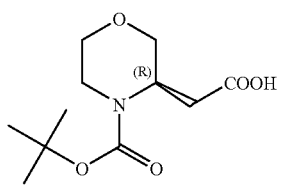

$C_{11}H_{19}NO_5$
M.: 245, 3 g. mol$^{-1}$ $[\alpha]_D^\circ = -35.7$ (c=1.94; $CH_2Cl_2$) M.p.: 82° C.

$^{13}$C MMR:

δ (CDCl$_3$) 175.9 (s, COOH), 154.5 (s, NCOOtBu), 80.5 (s, OC(CH$_3$)$_3$), 68.8 (s, OCH$_2$CH), 66.7 (s, OCH$_2$CH$_2$), 48.0 (s, OCH$_2$CH), 39.4 (s, OCH$_2$CH$_2$), 33.4 (s, CH$_2$COOH), 28.2 (s, OC(CH$_3$)$_3$).

$^1$NMR:

δ (CDCl$_3$) 175.9 (s, COOH), 154.5 (s, NCOOtBu), 80.5 (s, OC(CH$_3$)$_3$), 68.8 (s, OCH$_2$CH), 66.7 (s, OCH$_2$CH$_2$), 48.0 (s, OCH$_2$CH), 39.4 (s, OCH$_2$CH$_2$), 33.4 (s, CH$_2$COOH), 28.2 (s, OC(CH$_3$)$_3$).

Mass spectrometry:

M/Z (EI): 245 (7%) (M$^+$), 190 (10%), 172 (17%) (M-OC$_4$H$_9$)$^+$, 144 (3%), 172 (24%) ((M-C$_5$H$_9$O$_2$)$^+$), 142 (43%), 130 (14%), 114 (12%), 86 (31%), 70 (12%), 57 (100%) ((C$_4$H$_9$)$^+$), 41 (12%).

I.R.: (KBr) 3700-2500 ($\nu OH_{acid}$), 1713 ($\nu CO_{acid}$), 1694 ($\nu CO_{carbamate}$).

(3S)-4-tert-Butoxycarbonyl-3-carbethoxymethylmorpholine 3b

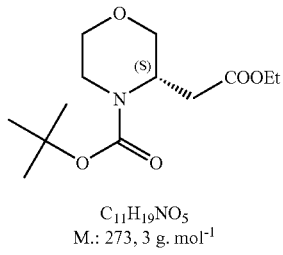

$C_{11}H_{19}NO_5$
M.: 273, 3 g. mol$^{-1}$ $[\alpha]_D^\circ = +35.6$ (c=1.15; $CH_2Cl_2$)

The enantiomeric excesses were measured by gas chromatography injection (Chirasil-DEX CB column):

Flow rate: helium 1 ml/min
T(oven): 150° C. isothermic.
tr=13.8 min for (S), 14.5 min for (R).

1.4. Identification of the Absolute Configuration of Compounds 3a and 3b by Synthesis of (3S)-3-(2-phenoxymethyl)morpholine hydrochloride

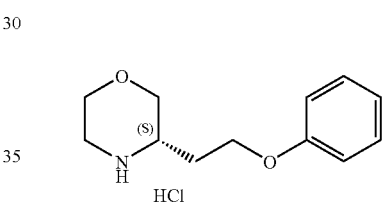

$C_{11}H_{21}NO_4$
M.: 243, 7 g. mol$^{-1}$ 4.2 ml of DiBAl—H (4.2 mmol, 2 equiv.) at −40° C. were added to a solution of 570 mg of β-amino ester 3b (2.1 mmol, 1 equiv.) in 20 ml of diethyl ether. The solution was stirred for 1 h at −40° C. and then for 1 h at ambient temperature. The mixture was hydrolyzed with a 0.5 N hydrochloric acid solution and the solution was then extracted with diethyl ether. The pooled organic phases were dried over magnesium sulphate. After evaporation of the solvents, the residue was purified by chromatography on silica gel; eluent: cyclohexane/ethyl acetate: 2/3. 390 mg of pure alcohol corresponding to the expected product were isolated yield=80%).

515 mg of diisopropylazodicarboxylate (2.55 mmol, 1.5 equiv.) at 0° C. were added to a solution of 390 mg of the preceding alcohol (1.7 mmol, 1 equiv.), of 160 mg of phenol (2.2 mmol, 1.3 equiv.) and of 670 mg of triphenylphosphine in 10 ml of THF. The mixture was stirred for 2 h 30 min at ambient temperature. After evaporation of the solvent, the residue was purified by chromatography on silica gel with, for eluent: cyclohexane/ethyl acetate: 4/1. 290 mg of pure ether corresponding to the expected product were isolated (yield 55%). This was heated at 50° C. for 12 h in a mixture of ethyl acetate and of a 3 M hydrochloric acid solution. After lyophilization, 145 mg of corresponding hydrochloride were isolated (yield: 63%).

$[\alpha]_D^{22}$=−8 (c=1.8; $H_2O$)
(litt. Brown, G. R. et al., *J. Chem. Soc. Perkin Trans. I* 1987, 547-551)
$[\alpha]_D^{22}$=+12 (c=1.74; $H_2O$) for the compound R.

EXAMPLE 2

Synthesis of Enantiopure Derivatives of pyrrolidine-2-acetic acid

Enzymatic racemate cleavage of 4

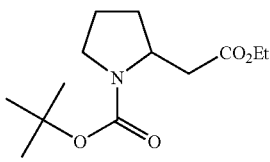

225 mg of PS Amano lipase were added to a solution of 303 mg of βamino ester 4 (1.18 mmol) obtained, starting with pyrrolidine, according to the procedures of Example 1, in 6 ml of water, 6 ml of ($10^{-2}$ M) buffer, pH 7, and 2 ml of THF. The pH was maintained at 7 by means of an auto-titrator, by adding a 0.1 N sodium hydroxide solution. After the addition of 6 ml of 0.1 N sodium hydroxide and stirring for 48 h, the solution was filtered and concentrated and the aqueous phase was then extracted with ether. The organic phases were pooled and dried over magnesium sulphate. After evaporation, 144 mg of ester 4b were obtained (yield: 47.5%). The aqueous phase was acidified to pH 3 and extracted with ether. The organic phases were pooled and dried over magnesium sulphate. After evaporation, 125 mg of 1-tert-butoxycarbonylpyrrolidine-2-acetic acid 4a were obtained (yield: 46.5%). The acid was recrystallized from hexane.

(2R)-1-tert-Butoxycarbonyl-2-carbethoxymethylpyrrolidine (4b)

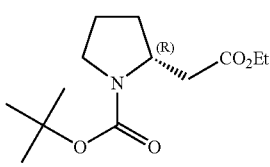

$[\alpha]_D^{20}$=+40.6 (c=2.50; $CH_2Cl_2$) lit. [1]$[\alpha]_D^\circ$=+44.1 (c=2.01; MeOH)
[1] Cassal, J. M; Fürst A.; Meier, W. *Helv. Chim Acta* 1976, 59, 1917-1924.

(2S)-1-tert-Butoxycarbonyl-2-carboxymethylpyrrolidine (4a)

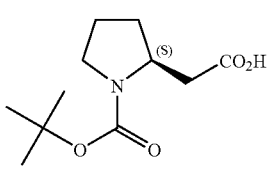

$C_{11}H_{19}NO_4$
M.: 229, 3g. $mol^{-1}$ $[\alpha]_D^{20}$=−38.6 (c=1.41; DMF) lit. [2] $[\alpha]_D^{20}$=−39.5 (c=1.9; DMF)
[2] Cassal, J. M.; Fürst A.; Meier, W. *Helv. Chim Acta* 1976, 59, 1917-1924.
M.p.=98° C. lit. [1]: M.p.=99-101° C.
[1] Cassal, J. M; Fürst A.; Meier, W. *Helv. Chim Acta* 1976, 59, 1917-1924.

$^{13}C$ NMR:
δ($CDCl_3$): 177.0 (s, COOR), 156.0 (s, $\underline{C}OOC(CH_3)_3$), 79.9 (s, $COO\underline{C}(CH_3)_3$), 53.9 (s, $\underline{C}HN$), 46.3 (s, $\underline{C}H_2CO_2H$ ou $\underline{C}H_2N$), 39.1 (s, $\underline{C}H_2CO_2H$ ou $\underline{C}H_2N$), 31.2 (s, $\underline{C}H_2CH$), 28.4 (s, $COOC(\underline{C}H_3)_3$), 23.5 (s, $\underline{C}H_2CH_2N$).

$^1H$ NMR:
δ($CDCl_3$) 4.34 (s large, 1H, $CH_2\underline{C}H$), 3.30 (m, 2H, $\underline{C}H_2N$), 2.80 (m, 1H de $C\underline{H}_2CO_2H$), 2.28 (dd, $^3J_{H-H}$=10 Hz, $^2J_{H-H}$=16 Hz 1H de $C\underline{H}_2CO_2H$), 2.00-1.79 (m, 4H, $C\underline{H}_2C\underline{H}_2CH$), 1.39 (s, 9H, $OC(C\underline{H}_3)_3$).

Mass spectrometry:
M/Z (EI) 229 (5%) (($M$)$^+$), 173 (24%) (($M-C_4H_8$)$^+$), 156 (26%) ($M-OC_4H_9$)$^+$), 128 (12%) (($M-CO_2C_4H_9$)$^+$), 114 (29%), 101 (3%), 82 (3%), 70 (97%), 57 (100%) (($C_4H_9$)$^+$), 41 (20%).

I.R.: (KBr) 3700-2800 ($\nu OH_{acid}$), 1735 ($\nu CO_{acid}$), 1655 ($\nu CO_{carbamate}$).

The enantiomeric excesses were measured on the ethyl ester by gas chromatography injection (Chirasil-DEX CB column):
Flow rate helium 1 ml/min
T(oven): 15⁰° C. isothermic
tr=9.8 min for (R), 10.1 min for (S).

EXAMPLE 3

Synthesis of Enantiopure Derivatives of pyrrolidine-2-acetic

The enantiopure pyrrolidine-2-acetic acid 4a and the corresponding enantiopure methyl ester 4c were obtained by the procedures of Example 1.

The table below gives the enantiomeric excesses obtained

| Example | Product | ee product (%) | Substrate | ee substrate (%) |
| --- | --- | --- | --- | --- |
| 1 | 3a | >99 | 3b | >99 |
| 2 | 4a | 94 | 4b | 99 |
| 3 | 4a | 99.1 | 4c | 99.4 |

The invention claimed is:
1. Process for producing enantiopure β-amino acid derivatives corresponding to general formula (I)

R1-NZ-CHR2-$CH_2$—COOR3    (I)

in which
R1 and R2 independently denote organic residues or R1 and R2 together form a cyclic substituent,
R3 denotes H or an organic residue, and
Z represents H or an amino function-protecting group,
comprising a step in which a mixture of enantiomers of a compound corresponding to general formula (II)

R1-NZ-CHR2-$CH_2$—COOR4    (II)

in which
R1, R2 and Z are as defined for formula (I), and
R4 is an organic residue,
is subjected to hydrolysis in the presence of a Pseudomonas cepacia lipase.

2. Process according to claim 1, in which the substituents R1 and R2 in the compounds of general formula (I) and (II) form a heterocycle with the group N-Z-CH.

3. Process according to claim 2, in which the heterocycle comprises at least one additional hetero atom.

4. Process according to claim 1, in which the substituent Z in the compound of general formula (II) is an amino function-protecting group.

5. Process according to claim 1, in which the substituent R4 in the compound of general formula (II) is a methyl or ethyl group.

6. Process according to claim 1, in which the hydrolysis is carried out at a temperature of 0° to 50° and a pH of 6 to 8.

7. Process according to claim 1, in which the amount of lipase used is 10 to 100 mg/mmol of compound of formula (II).

8. Process for producing a peptide or a peptide analogue, according to which
    (a) an enantiopure β-amino acid derivative is produced according to the process of claim 1;
    (b) the enantiopure β-amino acid derivative obtained is used to produce the peptide or the peptide analogue.

9. Process according to claim 1, in which the substituents R1 and R2 in the compounds of general formula (I) and (II) form a heterocycle with the group N-Z-CH, said ring comprising from 4 to 8 atoms.

10. Process according to claim 9, wherein said ring comprising from 5 to 7 atoms.

11. Process according to claim 2, wherein said hetero atom is N, O or S.

12. Process according to claim 1, in which the substituent Z in the compound of general formula (II) is an amino function-protecting group which is an alkoxycarbonyl group, an aryloxycarbonyl group or an aralkoxycarbonyl group.

13. The process according to claim 9, wherein said ring comprising from 5 to 6 atoms.

14. The process according to claim 1, wherein R3 is a linear or branched alkyl or alkylene group which may contain a hetero atom.

15. The process according to claim 14, wherein R3 is an alkyl group.

* * * * *